US012599450B2

(12) United States Patent
Duplat et al.

(10) Patent No.: US 12,599,450 B2
(45) Date of Patent: Apr. 14, 2026

(54) LIGHT PROPULSION FOR MICROROBOT

(71) Applicant: ROBEAUTE, Paris (FR)

(72) Inventors: Bertrand Duplat, Paris (FR); Quentin Francois, Paris (FR); Ali Oulmas, Paris (FR)

(73) Assignee: ROBEAUTE, Paris (FR)

( * ) Notice: Subject to any disclaimer, the term of this patent is extended or adjusted under 35 U.S.C. 154(b) by 292 days.

(21) Appl. No.: 18/575,506

(22) PCT Filed: Jun. 30, 2022

(86) PCT No.: PCT/EP2022/068110
§ 371 (c)(1),
(2) Date: Dec. 29, 2023

(87) PCT Pub. No.: WO2023/275272
PCT Pub. Date: Jan. 5, 2023

(65) Prior Publication Data
US 2024/0315788 A1 Sep. 26, 2024

(30) Foreign Application Priority Data
Jun. 30, 2021 (EP) .................................... 21305902

(51) Int. Cl.
*A61B 34/00* (2016.01)
*A61B 34/37* (2016.01)
*A61B 34/30* (2016.01)
(52) U.S. Cl.
CPC ........ *A61B 34/37* (2016.02); *A61B 2034/301* (2016.02)

(58) Field of Classification Search
None
See application file for complete search history.

(56) References Cited

U.S. PATENT DOCUMENTS

| | | |
|---|---|---|
| 2015/0298322 A1 | 10/2015 | Morris et al. |
| 2020/0237198 A1* | 7/2020 | Liu ........................ A61B 1/015 |
| 2020/0305796 A1 | 10/2020 | Robeaute |
| 2022/0160304 A1* | 5/2022 | Duplat ................. A61B 5/6847 |

FOREIGN PATENT DOCUMENTS

WO 2021053305 A1 3/2021

OTHER PUBLICATIONS

International Search Report issued on Oct. 11, 2022, in corresponding International Patent Application No. PCT/EP2022/068110, 3 pages.

* cited by examiner

*Primary Examiner* — Lynsey C Eiseman
(74) *Attorney, Agent, or Firm* — Maier & Maier, PLLC

(57) ABSTRACT
A microrobot including a propulsion system with a propulsion structure deformable in elongation/contraction along a main axis, an actuator or actuation zone configured to actuate sequentially elongation/contraction cycles of the propulsion structure, a light source aimed at, when activated, emitting at least one predetermined light signal, and a remote control unit. The light source includes an optical fiber, and is configured to be activated by the remote control unit, and the actuator or actuation zone is configured to be activated by the light signal emitted from the light source.

15 Claims, 6 Drawing Sheets

LIGHT PROPULSION FOR MICROROBOT

FIELD OF INVENTION

The present invention relates to a microrobot with a propulsion system, more particularly a light induced propulsion system, for navigating inside the human body.

BACKGROUND OF INVENTION

The ability to reach deep and functional structures without damage is a major challenge in mini-invasive surgery, especially in neurosurgery. Thanks to micro-technologies, it becomes possible to send a fully autonomous microrobot inside an organ of a subject, such as a brain. However, the propulsion of a microrobot in an environment at low Reynolds number, as is the brain, is a challenge because of absence of inertia and presence of relatively high drag forces due to the small size of the microrobot. Another important requirement is that the microrobot should be capable of moving in an organ while limiting as much as possible the physiological damage that its passage causes to the organ.

In this context, the invention is intended to propose a microrobot having a highly efficient propulsion mechanism in a fluid environment or a viscoelastic solid at low Reynolds number, while preserving as much as possible the integrity of the environment in which it is displaced.

This necessitates to have an as light and as small as possible microrobot inducing a minimal number of elements and pieces and very simple mechanisms.

SUMMARY

The present invention aims at solving this problem and thus relates to a microrobot configured to move in a viscous or viscoelastic navigation material, in particular inside the body of a subject, the microrobot comprising:
  a head portion and a rear portion, and
  a propulsion system,
wherein the propulsion system comprises:
  a propulsion structure comprising a deformable portion connecting the head portion and the rear portion, the deformable portion being deformable in elongation/contraction along a main axis connecting the head portion and the rear portion,
  an actuator or actuation zone configured to actuate sequentially elongation/contraction cycles of the deformable portion,
  a light source aimed at, when activated, emitting at least one predetermined light signal,
  a remote control unit,
wherein
  the light source comprises an optical fiber,
  the light source is configured to be activated by the remote control unit, particularly from outside the body of the subject, and
  the actuator or actuation zone is configured to be activated by the light signal emitted from the light source, the light signal thus actuating sequentially elongation/contraction cycles of the deformable portion, the microrobot being thus driven by light propulsion.

Thus, this solution achieves the above objective. In particular, it allows the obtaining of a very small microrobot with a propulsion displaying a very high volumetric power (power of the structure divided by its volume) as the physical and mechanical properties of photo-active materials are significantly better, at those sizes, than the solutions provided by the state of the art (such as electro-magnetic motors using magnets and coils). The invention further allows the obtention of a very simple to use and operate microrobot presenting an improved robustness with light as the single energy source for propulsion, and possibly as well as for steering, excluding the need to resort to other energy sources such as, for instance, electricity for an electromagnetic device using coils and magnets.

The device according to the invention may include one or more of the following characteristics, taken in isolation from one another or in combination with one another:
  the deformable portion may be a volumetric structure extending in 3D dimensions, said deformable portion being designed to allow any light signal to diffuse through it in any direction, at least when the deformable portion is in its elongated state,
  the contraction of the deformable portion when activated by the actuator or actuation zone may stop the light signal emitted from the light source to reach the actuator or actuation zone, thus leading to a deactivation of the actuator or actuation zone and thus to an elongation of the deformable portion,
  the light source is directly connected to the microrobot,
  the connection between the microrobot and the light source may be a hermetic connection,
  the optical fiber may comprise at least one sensor in order to sense the light signal running along said optical fiber,
  the at least one sensor may communicate with the remote control unit in order to modulate the emitted light signal as a function of the received light signal by each actuator or actuation zone,
  the actuator or actuation zone may comprise a light focalizing element in order to focalize the emitted light signal,
  the propulsion system may further comprise a steering system, the propulsion structure thus comprising at least one steering element connected to the head portion and the rear portion, said at least one steering element being activable by the light signal emitted by the light source,
  the at least one steering element may extend along the deformable portion,
  the at least one steering element may be part of the deformable portion,
  the system may further comprise a light dispatching device, said light dispatching device being controlled by the remote control unit in order to dispatch the light emitted by the light source between the actuator or actuation zone, the at least one steering element and any further light activable element,
  the electromagnetic properties of the light signal able to activate the actuator or actuation zone and the electromagnetic properties of the light signal able to activate the at least one steering element may be different from each other,
  the propulsion structure may comprise several steering elements, each steering element being activable by a light signal with a specific set of electromagnetic properties, each set of electromagnetic properties being different one from the others,
  the system may further comprise an external anchoring element, said external anchoring element being aimed at being secured to the external surface of the body of the subject, the light source and the microrobot being connected to the external anchoring element.

BRIEF DESCRIPTION OF THE DRAWINGS

The invention will be better understood, and other aims, details, characteristics and advantages thereof will emerge more clearly on reading the detailed explanatory description which follows, of embodiments of the invention given by way of illustration, purely illustrative and non-limiting examples, with reference to the accompanying drawings.

DETAILED DESCRIPTION

Figure 1:
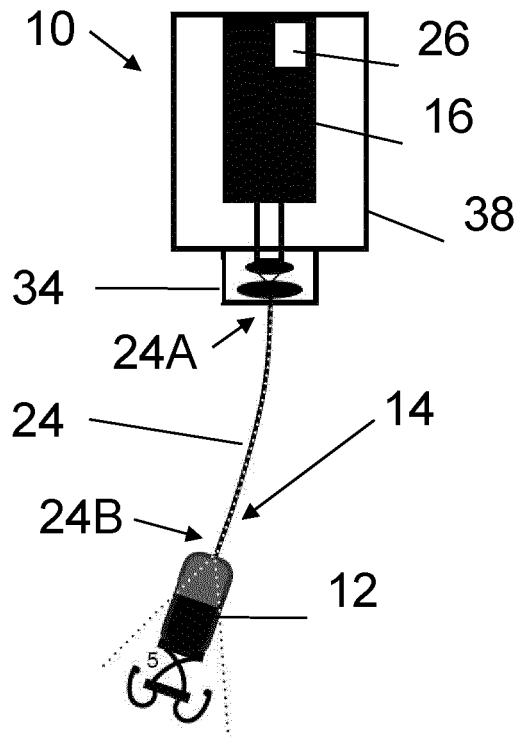
FIG. 1 is a schematic general view of the propulsion system according to a first embodiment of the present invention.

As can be seen on FIG. 1, the microrobot 12 according to the present invention comprises a propulsion system 10 including:

a light source 14, and
a remote control unit 16.

More precisely, the microrobot 12 is configured to move in a viscous or viscoelastic material, in particular inside the body of a subject.

In materials science and continuum mechanics, viscoelasticity is the property of materials that exhibit both viscous and elastic characteristics when undergoing deformation. Viscous materials, like water, resist shear flow and strain linearly with time when a stress is applied. Elastic materials strain when stretched and immediately return to their original state once the stress is removed. Where the viscosity is naturally high, such as polymer solutions and polymer melts, flow is normally laminar.

Viscoelastic materials have elements of both of these properties and, as such, exhibit time-dependent strain. Whereas elasticity is usually the result of bond stretching along crystallographic planes in an ordered solid, viscosity is the result of the diffusion of atoms or molecules inside an amorphous material.

Figure 2:
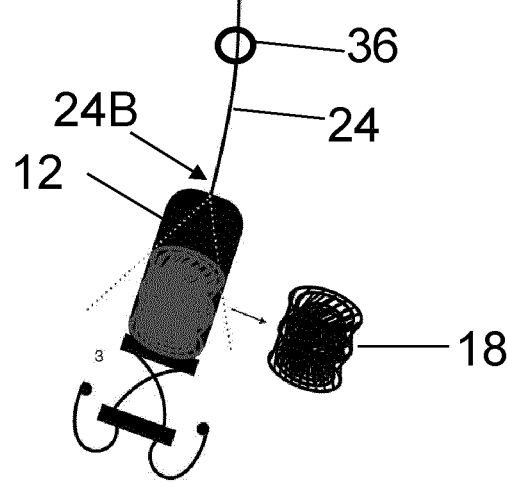
FIG. 2 is a schematic view of a microrobot according to the invention.
Figure 4:
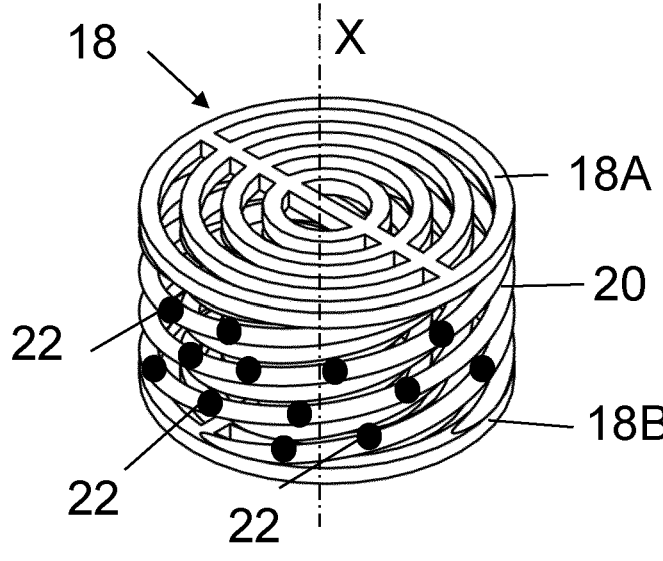
FIG. 4 is a view in perspective of a propulsion structure according to a second embodiment.

As can be seen on FIG. 2, the microrobot 12 comprises:

a propulsion structure 18, detailed, for example, on FIG. 4, comprising a head portion 18A, a rear portion 18B and a deformable portion 20 connecting the head portion 18A and the rear portion 18B, and an actuator or actuation zone 22 comprising a light-actuated-material which is deformed by light actuation.

The deformable portion 20 of the propulsion structure 18 is deformable in elongation/contraction along a main axis X connecting the head portion 18A and the rear portion 18B.

Figures 5A, 5B:
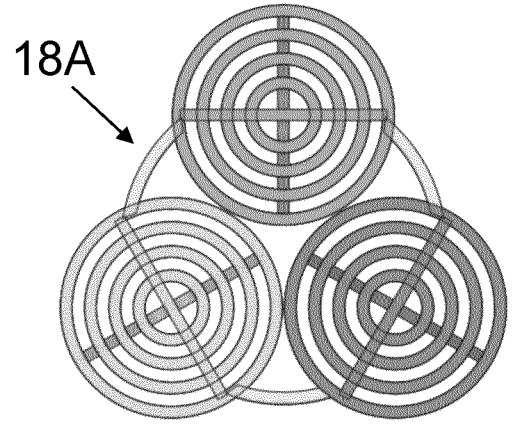
FIG. 5a is a view from above of a propulsion structure and a steering system according to a third embodiment.
FIG. 5b is a view in perspective of a propulsion structure and a steering system according to the third embodiment.

Preferably, the deformable portion 20 of the propulsion structure 18 is a volumetric structure extending in 3D dimensions (see FIGS. 4 and 5b). More particularly, the deformable portion 20 is a volumetric holed structure extending in 3D dimensions. On the particular embodiments illustrated in FIGS. 4 and 5b, the deformable portion 20 is a series of three spring alike structures fitted in each other, the first spring alike structure surrounding the second spring alike structure which surrounds the third spring alike structure. The structure of the deformable portion 20 is designed to allow any light signal to diffuse through it in any direction, at least when the deformable portion 20 is in its elongated state. As a volumetric holed structure is made of a very important number of interlacing surfaces, when a light signal hits this sort of volume, it hits a very high number of surface(s), a significant higher amount than compared to a plain volumetric structure or a single 2D surface structure. In addition, the structure's deformable portion is able to sustain a very high number of contraction/elongation cycles without losing its properties.

In the embodiment depicted in FIGS. 5a and 5b, the deformable portion 20 comprises three independent parts which can each be contracted and/or elongated each one independently from the others. The actuation of one part can thus be independent from the actuation of the others.

Thus, regarding the propulsion structure 18, the aim of the present invention is to maximize the surface and volume of the structures directly exposed to a light signal, knowing that, on the first hand, light is absorbed by the material and that, on the second hand, after a certain distance from the surface the light beam loses most of its power.

The power of mechanical actuation (volumetric power) of a light-actuated-material is very weak at centimetric and above dimensions. At those dimensions, it cannot compete with electromagnetic engines (made with magnets and/or coils) for instance. However, at smaller dimensions including nanometric, micrometric and sub-millimetric dimensions, this type of engine becomes interesting with a good volumetric power ratio. This volumetric power ratio is offered by the specific shape of the volumetric holed structure of the deformable portion 20 illustrated in FIGS. 4 and 5b.

Further, a kind of structure as illustrated on FIGS. 4 and 5b can display a much high contraction power than a single spring alike structure. The mechanical power of each subpart of the propulsion structure 18 contributes to the optimized power of the whole system 10 which generates the propulsion movement of the complete structure. Example of such structures that maximizes the power (and the responsiveness to any kind of light signal): honeycombs, multiple volume spirals (see FIGS. 4 and 5b) and, fractal branches/leaf, etc.

The actuator or actuation zone 22, part of the deformable portion 20, is configured to transform light excitation into sequential elongation/contraction cycles of the whole deformable portion 20.

The actuator or actuation zone 22 may be regularly distributed around the main axis X to induce repeated deformations, symmetric around the main axis X, in contraction/elongation along the main axis X of the whole deformable portion 20 upon activation by the light excitation. These deformations cause, directly or indirectly, the microrobot to move along a direction within the viscous or viscoelastic material.

The actuator or actuation zone 22 may for example comprise Liquid crystalline networks (LCNs). Typically, Liquid Crystalline Networks, when properly configured chemically and spatially, contract in a direction under the effect of light-because of at least one of direct light effect and indirect heat effect induced by the light, and elongate back when the light- and/or light-induced heat, go down certain threshold. At the molecular level, it is due to ability of each monomer included in the polymer to shift shape and contract under light- and/or the induced heat- and then get back to their elongated shape. The proper alignment of polymer strings leverage this effect at the scale of the whole structure (potentially macroscopic).

Alternatively or in a complementary manner, the actuator or actuation zone 22 may comprise:

LCEs (Liquid crystalline elastomers)

azo-polyurea polymer (azo-PU),

The LDLCF (light-driven liquid-crystal film), containing azobenzene chromophores can be bent by UV light and recovered by white light.

Possibly the deformable portion 20 of the propulsion structure 18 is entirely made of the aforementioned photosensitive material, the actuator or actuation zone 22 extending over all the deformable portion 20.

The actuator or actuation zone 22 is configured to be activated by the light emitted from the light source 14, directly and/or indirectly though heat generated by light. This way, the light signal emitted by the light source 14 is actuating sequentially elongation/contraction cycles of the deformable portion 20 of the propulsion unit 18. This leads the microrobot 12 to be driven by light propulsion, possibly with steering also driven by light as it will become apparent from the following of the description.

In one embodiment, the head portion 18A of the propulsion structure 18 comprises at its surface a plurality of propulsion cilia (not represented), configured to interact with the viscous material in which the microrobot 12 navigates. In some embodiment, the rear portion 18B also comprises at its surface a plurality of propulsion cilia (not represented) that are identical to the propulsion cilia of the head portion 18A. In those embodiments, the sequential elongation/contraction cycles of the deformable portion 20 actuated by the actuator or actuation zone 22 cause a displacement of the propulsion cilia in the viscous material, thus producing a propulsive force, which results in a movement of the microrobot 12.

Although disclosed in relation with a propulsion structure, acting as a micro-engine, in which the axial deformation of the deformable portion 20 causes a movement of cilia which in turns causes a movement of the microrobot, the invention is not limited to such embodiment. For example, the propulsion structure could act as a rotary micro-engine of the kind disclosed in document WO 2022/008729. The deformations in elongation/contraction along the main axis of the deformable portion under the effect of light would then cause rotation of a platform to which a propulsion arrangement of any suitable kind, such as a propeller, is attached so that the microrobot moves within the viscous material.

Figure 3:
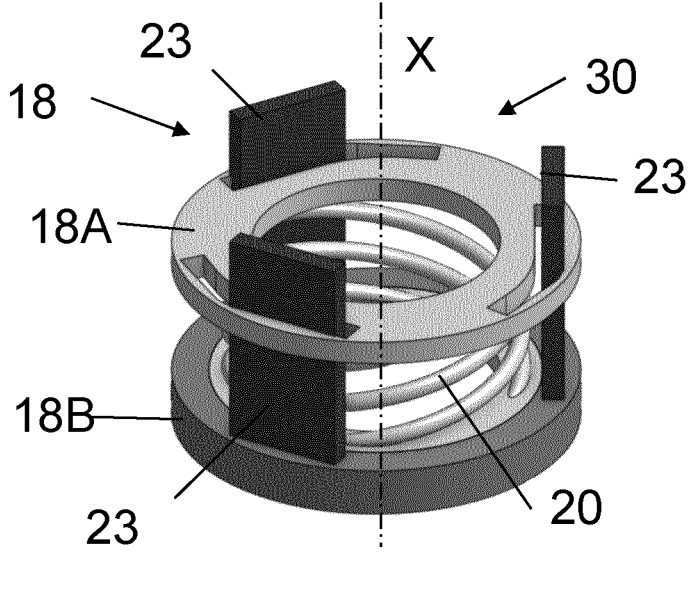
FIG. 3 is a view in perspective of a propulsion structure and a steering system according to a first embodiment.

The embodiment depicted on FIG. 3 displays a deformable portion 20 surrounded by three actuators 23. Each actuator 23 extends axially, along the main elongation axis X between the head portion 18A and the rear portion 18B of the propulsion unit 18. When the actuators 23 are activated, they contract and their length reduces, leading the head portion 18A and the rear portion 18B to come closer to each other, thus contracting the propulsion unit 18.

In the embodiment illustrated on FIG. 4, the deformable structure 20 comprises a series of actuation zones 22 which contract under light excitation and are distributed along the strings of said deformable structure 20. The activation of all those actuation zones 22 induces a global contraction of the deformable portion 22. When the light source is shut down, the actuation zones 22 expand back to their rest shape (for instance with LCN materials).

In the embodiment illustrated on FIG. 5b, the deformable structure 20 and the actuator/actuation zone 22 are the same element: the deformable structure 20 is entirely comprised within the actuation zone 22.

Regarding the two last embodiments, it is particularly important that the structure of the deformable portion 20 allows any emitted light signal to reach any possible surface of the actuation zones 22. It is thus very important to have as many available surfaces as possible to be reached by the light signal, enabling a powerful, homogeneous and coherent activation of the deformable structure 20, underlying the relevancy of a series of fitting spring alike structures as illustrated in FIGS. 4 and 5b.

The light source 14 is aimed at, when activated, emitting at least one predetermined light signal. This predetermined light signal is defined by a given wave length, a given polarization, a given power, a given frequency, etc. The light source 14 is configured to be activated by the remote control unit 16, particularly from outside the body of the subject, in order to send the predetermined light signal to or on the actuator or actuation zone 22 of the propulsion unit 18. The speed of the microrobot is thus controlled by light signal modulation. This modulation is enabled by the remote control unit 16 and can be controlled by a user by means of said remote control unit 16. Said modulation may for example be an amplitude modulation and it might be a sinusoidal signal modulation or a square wave signal modulation or even a saw tooth signal modulation or any other likewise signals.

As can be seen on FIGS. 1, 2, 6, 7, 8a and 8b, the light source 14 comprises an optical fiber 24. Since light does not pass efficiently inside body and brain tissues, the system 10 comprises an optical fiber 24 to bring the light signal to the light actuated materials of each actuator or actuation zone 22. The optical fiber 24 has a first end 24A and a second end 24B.

An optical fiber is a flexible, transparent fiber made by drawing glass (silica) or plastic to a diameter slightly thicker than that of a human hair. Optical fibers are used most often as a means to transmit light between the two ends of the fiber and find wide usage in fiber-optic communications, where they permit transmission over longer distances and at higher bandwidths (data transfer rates) than electrical cables.

The optical fiber 24 regarding the present invention has to be sufficiently thick in diameter to transmit enough power to the actuator(s) actuating zone(s) 22 (and thus to the light activable propulsion structure 18) and sufficiently thin in diameter to be light and flexible enough not to impede on the microrobot 12 self-propelled motions.

Thus, regarding the present invention, the optical fiber 24 links, directly or indirectly, each actuator or actuation zone 22 to a primary light source 26 which is located outside the body of the subject, for example located inside the remote control unit 16. Said primary light source 26 is for example a laser light or a UV light or a Led.

The first extremity 24A of optical fiber 24 is thus connected, preferably secured, to said primary light source 26 and the second extremity 24B of the optical fiber 24 brings the light signal inside the body of the subject, to each actuator or actuation zone 22. In some embodiments, the second extremity 24B of the optical fiber 24 activates the actuator(s) or actuation zone(s) from a given distance of the microrobot 12 (see FIGS. 7, 8a, 8b) meaning that the second extremity 24B of the fiber optic 24 is a free end moving freely within the navigation material. In those embodiments, the light signal has to cross some of the navigation material before reaching each actuator or actuation zone 22.

Figure 6:
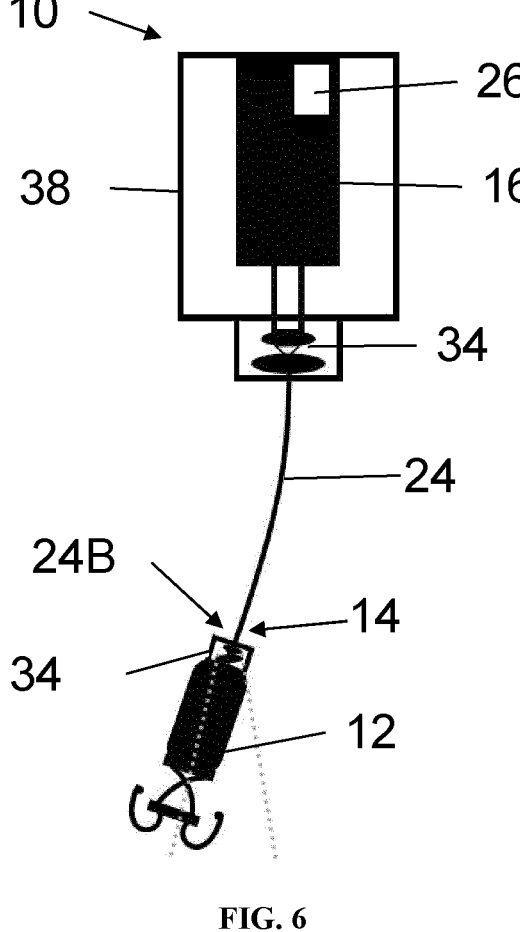
FIG. 6 is a schematic general view of the propulsion system according to a second embodiment of the present invention.
Figure 7:
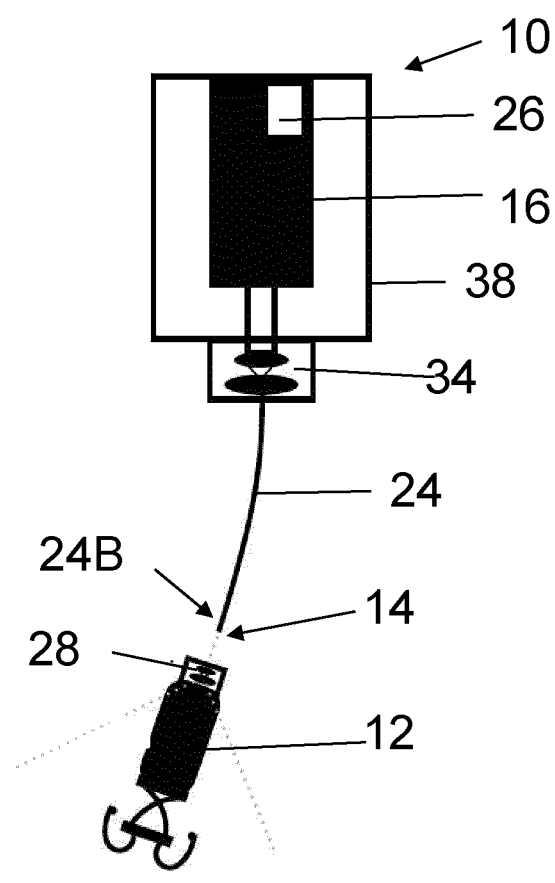
FIG. 7 is a schematic general view of the propulsion system according to a third embodiment of the present invention.

In some other embodiments, the second extremity 24B of the optical fiber 24 is or directly connected or secured to microrobot 12, preferably to the rear end of the microrobot 12 (see FIGS. 1, 2 and 6). This might be necessary when the microrobot 12 has to navigate through very dark or very viscous fluids which highly absorb light. As an example, this connection can be achieved with a light waveguide embarked on the microrobot. Typically such guides, often made of glass fibers, can have diameters of a few tenth of micrometers, and potentially below ten micrometers.

In any embodiment, but particularly when the optic fiber 24 is directly connected or secured to the microrobot 12, the connection between the microrobot 12 and the light source 14 can be a hermetic connection. This avoids any light diffusion inside the navigation material.

In some embodiments, particularly the embodiments in which the second extremity 24B of the optical fiber 24 is a free end, the microrobot comprises a light focalizing element 28 (see FIG. 7) in order to focalize or refocalize the emitted light signal before it hits the actuator(s) or actuation zone 22. This optical fiber 24 might for example comprise a lens.

In some embodiments, the propulsion system 10 further comprises a steering system 30 and/or a tool activation system (not represented). In some embodiments, the microrobot 12 may comprise some tools or elements (such as pili, cilia, flagella, fins, tails, legs, screws, etc.) which might also be activable by an emitted light signal.

The advantage of having a propulsion structure 18 distinct (or largely distinct) from the other propulsion parts (like the propulsion cilia) detailed previously, is to pack more power in a small volume. The subsequent advantage of having a direct control on the propulsion structure 18 itself, distinct of the other structures, is that if the power packed into the propulsion structure 18 remains sufficient even if the whole system 10 displays a very small volume.

The steering system 30 comprises at least one steering element 32, in the embodiments depicted on FIGS. 3, 5a and 5b, there are three steering elements 32 to be seen. As can be seen on those figures, in those embodiments, the propulsion structure 18 comprises at least one steering element 32 connected to the head portion 18A and the rear portion 18B. In the embodiment illustrated on FIG. 3, the steering elements 32 extend along the main axis X along the deformable portion 20. In the embodiment of FIGS. 5a, 5b, each steering element is a deformable part of the deformable portion 20. In both embodiments, the actuator(s) or actuation zone(s) 22 comprise the steering elements 32. More precisely, the set of steering elements 32 forms the actuator(s) or actuation zone(s) 22.

Regardless of the embodiment, the light signal emitted by the light source 14 activating the propulsion and also activates each steering element 32. However, the electromagnetic properties of the light signal able to activate each actuator or actuation zone 22 and the electromagnetic properties of the light signal able to activate the at least one steering element 32 are different from each other. More particularly, the propulsion structure 18 comprises several steering elements 32, each steering element 32 being activable by a light signal with a specific set of light electromagnetic properties each specific set of light electromagnetic properties being different one from the others.

The aim of the steering element 32 is to allow a steering of the microrobot 12 with the navigation material based on the same light beam brought on the microrobot by the optical fiber. More particularly to allow to propel and steer the microrobot 12 within the navigation material by means of the single light signal modulation. This modulation is enabled by the remote control unit 16 and can be controlled by a user by means of said remote control unit 16. Said modulation may for example be, like for the speed control, an amplitude or a frequency modulation and it might be a sinusoidal signal modulation or a square wave signal modulation or even a saw tooth signal modulation as well as similar oscillating signals.

In order to enable the steering to take place, each steering element 32 has to be activable independently of the others. In this regard, the propulsion system 10 may further comprise a light dispatching device 34. This light dispatching device 34 is controlled by the remote control unit 16. In some embodiments (see FIGS. 1, 7, 8a and 8b), this light dispatching device 34 comprises one part which is either located at the primary light source 26 or in/on the microrobot on the way of the light signal. In some other embodiment (see FIG. 6), the light dispatching device 34 comprises two parts, the first one being located at the primary light source 26 and the second part being located in/on the microrobot on the way of the light signal. This light dispatching device 34 enables dispatch the light signal emitted by the light source 14 between the actuator(s) or actuation zone(s) 22, the at least one steering element 32 and any further light activable element (not represented) of the propulsion system 10, the steering system 30 and the tool activation system.

To do so, the light dispatching device 34 has, in addition to the already mentioned light signal modulation possibilities, a physical effect on the emitted light signal: it can change its light electromagnetic properties on demand.

For example, as can be seen on FIG. 6 in which the light dispatching device 34 changes the direction of the light signal, by means of a mirror system, in order to hit only one selected steering element 32 thus inducing a dissymmetrical contraction of the deformable portion and thus, inducing a rotation of the microrobot 12 within the navigation material. This kind of dispatching might be particularly efficient regarding a steering device as illustrated on FIGS. 5a and 5b in which each steering element 32 can thus be contracted at a different time or at a different intensity thus allowing a very precise control of the navigation of the microrobot 12. In some other embodiments, the light dispatching device 34 can change the wavelength, the frequency or the polarization of said emitted light signal in order to activate a specific activable element.

The steering and speed of the microrobot 12 is thus controlled by means of a light signal modulation, mostly an amplitude modulation. For example, this enables the system to use the addition of a sinusoidal and a constant to drive the steering and the propulsion, respectively.

In some embodiments, in addition to the signal modulation control, the contraction of the deformable portion 20 when activated by the actuator or actuation zone 22 stops any light signal emitted from the light source 14 to reach the actuator or actuation zone 22. This leads to a deactivation of the actuator or actuation zone 22 and thus to an elongation of the deformable portion 20. In the elongated state, the actuator(s) or actuation zone(s) 22 is/are available to the emitted light signal again, leading thus to a contraction of said deformable portion. This contraction leading to an elongation, and vice-versa, one cycle follows another.

In some embodiments, the optical fiber 24 comprises at least one sensor 36 (see FIG. 2) in order to sense either the light signal running along the optical fiber 24 from its first extremity 24A to its second extremity 24B and/or the full 3D shape of the overall fiber optics.

It may happen that, following the navigation of the microrobot 12 inside the navigation material, that the optical fiber 24 forms an inconvenient angle which may lead to a weakening of the light signal reaching the actuator(s) or actuation zone(s) or steering element(s) 32 of the propulsion system 10. In order to avoid a bad signal communication, the at least one sensor 36 thus communicated, in real time, with the remote control unit 16 in order to modulate the emitted light signal as a function of the received light signal by each actuator or actuation zone 22. This way, when the effect induced by the received light signal does not correspond to the effect that should have been induced by the emitted light signal (meaning that it does not induce the effect it is supposed to induce due to signal alteration), an operator (including an algorithm) may increase the power or the clarity (for example) of the emitted light signal in order to obtain the desired effect and to avoid any unwanted motion of the microrobot 12. It can be modulated with either the measure of the light characteristics at 24B or using the real-time shape deformation of the fiber optics, known through either sensors or imagery (Scanners, MRI, Echograph) an optical simulation is able to calculate the signal received by the propulsion system and modulate the initial light signal according to the expected outcome.

The at least one sensor 36 may also be used in combination with medical imagery to follow, in real time, the movements of the optical fiber 24 inside the navigation material.

Figures 8A, 8B:
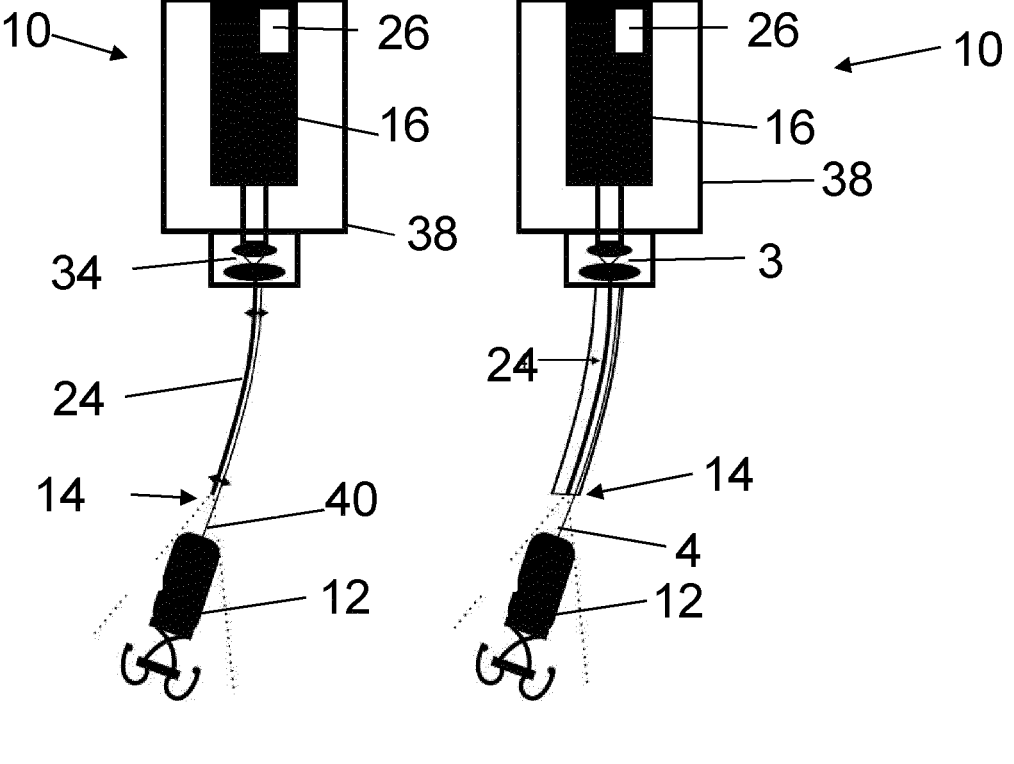
FIG. 8a is a schematic general view of the propulsion system according to a fourth embodiment of the present invention.
FIG. 8b is a schematic general view of the propulsion system according to a fifth embodiment of the present invention.

In some embodiments, as can be seen on FIGS. 8a and 8b, the propulsion system 10 comprises an external anchoring element 38. This external anchoring element 38 aims at being secured to the external surface of the body of the subject. The light source 14 (particularly the primary light source 26) and the remote control unit 16 may be connected to this external anchoring element 38.

In those embodiments, the microrobot 12 is secured to the external anchoring element 38 by means of a retrieval cable 40, which aims at improving the safety of the system 10. The optical fiber 24 might be secured to this cable 40 (see FIG. 8a). In other embodiments, the light source 14 is connected to the external anchoring element 38 and to the retrieval cable 40 by means of a catheter.

The microrobot 12 is able to move in 3D in the navigation material thanks to a single light source through two light-activated microsystems: the propulsion for the forward/backward degree of freedom and the steering for the 3D orientation, without any need to resort to any other source of energy than the light for both propulsion and steering.

The invention claimed is:

1. A microrobot configured to move in a viscous or viscoelastic navigation material, the microrobot comprising:
   a head portion and a rear portion, and
   a propulsion system, wherein the propulsion system comprises:
      a propulsion structure comprising a deformable portion connecting the head portion and the rear portion, the deformable portion being deformable in elongation and contraction along a main axis connecting the head portion and the rear portion,
      an actuator or actuation zone configured to actuate sequentially elongation and contraction cycles of the deformable portion,
      a light source aimed at, when activated, emitting at least one predetermined light signal, and
      a remote control unit,
   wherein:
      the light source comprises an optical fiber, the light source is configured to be activated by the remote control unit, and
      the actuator or actuation zone is configured to be activated by the light signal emitted from the light source, the light signal thus actuating sequentially elongation and contraction cycles of the deformable portion, the microrobot being thus driven by light propulsion.

2. The microrobot according to claim 1, wherein the deformable portion is a volumetric structure extending in 3D dimensions, said deformable portion being designed to allow any light signal to diffuse through it in any direction, at least when the deformable portion is in its elongated state.

3. The microrobot according to claim 1, wherein the contraction of the deformable portion when activated by the actuator or actuation zone stops the light signal emitted from the light source to reach the actuator or actuation zone, thus leading to a deactivation of the actuator or actuation zone and thus to an elongation of the deformable portion.

4. The microrobot according to claim 1, wherein the light source is directly connected to the microrobot.

5. The microrobot according to claim 4, wherein the connection between the microrobot and the light source is a hermetic connection.

6. The microrobot according to claim 1, wherein the optical fiber comprises at least one sensor in order to sense the light signal running along said optical fiber.

7. The microrobot according to claim 6, wherein the at least one sensor communicates with the remote control unit in order to modulate the emitted light signal as a function of the received light signal by each actuator or actuation zone.

8. The microrobot according to claim 1, wherein the actuator or actuation zone comprises a light focalizing element in order to focalize the emitted light signal.

9. The microrobot according to claim 1, wherein the propulsion system further comprises a steering system, the propulsion structure thus comprising at least one steering element connected to the head portion and the rear portion, said at least one steering element being activable by the light signal emitted by the light source.

10. The microrobot according to claim 9, wherein the at least one steering element extends along the deformable portion.

11. The microrobot according to claim 9, wherein the at least one steering element is part of the deformable portion.

12. The microrobot according to claim 11, wherein the system further comprises a light dispatching device, said light dispatching device being controlled by the remote control unit in order to dispatch the light emitted by the light source between the actuator or actuation zone, the at least one steering element and any further light activable element.

13. The microrobot according to claim 11, wherein the electromagnetic properties of the light signal able to activate the actuator or actuation zone and the electromagnetic properties of the light signal able to activate the at least one steering element are different from each other.

14. The microrobot according to claim 13, wherein the propulsion structure comprises several steering elements, each steering element being activable by a light signal with a specific set of electromagnetic properties, each set of electromagnetic properties being different one from the others.

15. The microrobot according to claim 1, wherein the system further comprises an external anchoring element, said external anchoring element being aimed at being secured to the external surface of the body of the subject, the light source and the microrobot being connected to the external anchoring element.

* * * * *